United States Patent [19]

Townsend et al.

[11] B 4,008,282

[45] Feb. 15, 1977

[54] PREPARATION OF TRIARYL PHOSPHINES

[75] Inventors: John Melvin Townsend, Belleville; Donald Herman Valentine, Jr., Westfield, both of N.J.

[73] Assignee: Hoffmann-La Roche Inc., Nutley, N.J.

[22] Filed: Oct. 29, 1974

[21] Appl. No.: 518,326

[44] Published under the second Trial Voluntary Protest Program on March 23, 1976 as document No. B 518,326.

Related U.S. Application Data

[63] Continuation-in-part of Ser. No. 425,012, Dec. 14, 1973, abandoned.

[52] U.S. Cl. .......................................... 260/606.5 P
[51] Int. Cl.$^2$ ........................................... C07F 9/02
[58] Field of Search ............................ 260/606.5 P

[56] References Cited

UNITED STATES PATENTS

| | | | |
|---|---|---|---|
| 3,261,871 | 7/1966 | Fritzsche et al. | 260/606.5 P |
| 3,280,195 | 10/1966 | Fritzsche et al. | 260/606.5 P |
| 3,342,871 | 9/1967 | Maier | 260/606.5 P |
| 3,405,180 | 10/1968 | Natoli | 260/606.5 P |
| 3,496,235 | 2/1970 | Maier | 260/606.5 P |
| 3,534,104 | 10/1970 | Maier | 260/606.5 P |
| 3,780,111 | 12/1973 | Young et al. | 260/606.5 P |

OTHER PUBLICATIONS

Fritzsche et al., Chem. Ber. vol. 97, pp. 1988–1993 (1964).

*Primary Examiner*—Helen M. S. Sneed
*Attorney, Agent, or Firm*—Samuel L. Welt; Bernard S. Leon; William H. Epstein

[57] ABSTRACT

The conversion of triaryl phosphine oxide to the corresponding phosphine by reduction with hydrogen utilizing sulfur or selenium as the catalyst wherein said reduction is carried out in the presence of silicon tetrahalide.

14 Claims, No Drawings

PREPARATION OF TRIARYL PHOSPHINES

Cross Reference to Related Applications

This application is a continuation in part of our U.S. application Ser. No. 425,012 filed Dec. 14, 1973, now abandoned.

BACKGROUND OF THE INVENTION

Triaryl phosphines have proven to be extremely useful in Wittig reactions. During the course of the Wittig reactions, these phosphines are converted to phosphine oxides which are of little use commercially. The number of Wittig type reactions which are being utilized has created a problem with regard to the disposal of the phosphine oxides produced as waste products during this reaction. Furthermore, the phosphine starting materials are rather expensive. The cost of the phosphine starting material coupled with the expense of disposing of the phosphine oxide waste products has proven disadvantageous in commercial Wittig processes. Therefore, there has been a search for an economic means for converting these phosphine oxide waste products back into the phosphine starting materials.

In the past, triaryl phosphine oxides have been converted to the corresponding phosphines by a number of methods such as by treatment with hydrohalosilanes, as described in U.S. Pat. No. 3,261,871, or by first converting the triaryl phosphine oxides into the corresponding phosphine halides and then treating these halides with a reducing metal or phosphorous to form the triaryl phosphine, as described in U.S. Pat. No. 3,405,180 and in U.S. Pat. No. 3,481,988. It has also been disclosed in U.S. Pat. No. 3,280,195 Fritzche et al. Oct. 13, 1966 that phosphine oxides can be reduced to phosphines by utilizing either a reducing metal or hydrogen in the presence of a metal catalyst. In this process, a silicon tetrahalide has been utilized as an auxiliary agent in the reduction.

Furthermore, other specialized reducing agents such as phenyl trihydrosilane, triphenylhydrosilane, methyl polysiloxane, hexachlorodisilane, have been utilized to reduce triaryl phosphine oxides to triaryl phosphines. However, methods for reducing the triaryl phosphine oxides to the corresponding phosphines with conventional reducing agents have met with little success. In many cases, the use of these conventional reducing agents results in the conversion of triaryl phosphine oxide to the corresponding diaryl phosphine. Previous use of catalytic hydrogenation conditions gave ring hydrogenated products rather than deoxygenation. In addition, the use of some conventional reducing agents to reduce these triaryl phosphine oxides requires extreme conditions of heat and pressure in order to carry out the reduction of the triaryl phosphine oxides. Therefore, the use of conventional reducing agents to carry out the reduction of phosphine oxides to the corresponding phosphines has not proven to be entirely satisfactory and commercially feasible.

SUMMARY OF THE INVENTION

In accordance with this invention, it has been found that a phosphine oxide of the formula:

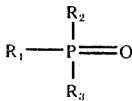   I wherein $R_1$, $R_2$ and $R_3$ are aryl; can be converted to the corresponding phosphine of the formula:

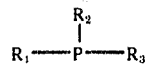   II wherein $R_1$, $R_2$ and $R_3$ are as above; by reacting the phosphine oxide of formula I with hydrogen utilizing a sulfur or selenium catalyst in the presence of an auxiliary agent with is tetrahalosilane.

In accordance with this invention, it has been found that with the sulfur and selenium catalyst, use of the aforementioned auxiliary agents allows the compound of formula I to be converted to the compound of formula II without utilizing extreme elevated conditions of temperature and pressure. The process of this invention allows one to carry out the formation of the compound of formula II in higher yields with faster reaction rates and higher percent conversion than that obtained heretofore. It has been found that these catalysts and these auxiliary agents allow the reduction to be carried out without the formation of undesired by-products such as diaryl phosphine or ring hydrogenated products. If sulfur or selenium catalysts are used, which are metal catalysts having sulfur or selenium incorporated therein, the yields are approximately quantitative. Therefore, the process of this invention provides an efficient and economic method for reducing triaryl phosphine oxides to the corresponding triaryl phosphine.

DETAILED DESCRIPTION OF THE INVENTION

The term "halogen" as used throughout the instant specification designates chlorine, bromine and iodine, with chlorine being preferred. The term "aryl" designates aromatic hydrocarbon radicals containing from 6 to 16 carbon atoms. These aryl radicals include phenyl, tolyl, xylyl, and naphthyl. Among the preferred aryl radicals are the lower alkyl substituted aryl radicals such as tolyl.

The reaction of this invention can be carried out with any tertiary aryl substituted phosphine oxide to produce the corresponding tertiary aryl substituted phosphine. Among the many phosphines that can be prepared by the process of this invention are the following:
triphenylphosphine;
trixylylphosphine; and
tritolylphosphine.

In accordance with this invention, the phosphine oxide of formula I is reacted with hydrogen in the presence of sulfur or selenium and an auxiliary agent such as tetrahalosilane to produce the phosphine of formula II. Among the preferred auxiliary agents is tetrachlorosilane.

Sulfur or selenium can be added to the reaction mixture as elemental sulfur or selenium. Any sulfur or selenium compound capable of acting as a sulfur or selenium atom donor may also be used. Among the preferred sulfur compounds are inorganic sulfides such as alkali metal sulfides (e.g. sodium sulfide) and hydrogen sulfide; organic sulfur compounds such as mercaptans, sulfides, episulfides, etc., such as t-butyl mercaptan and ethylene episulfide. An especially preferred sulfur compound is the triaryl phosphine sulfide corresponding to the triaryl phosphine oxide of formula II which is to be converted to the phosphine of formula I.

Selenium can be introduced as elemental selenium, inorganic selenides such as sodium selenide or hydrogen selenide, or organic selenium compounds such as selenols and selenide. An especially preferred organic selenium compound is triaryl phosphine selenide.

Sulfur or selenium alone can be used to catalyze the reaction of the triaryl phosphine oxide of formula II with hydrogen and tetrahalosilane to give the triaryl phosphine of formula I. If desired, however, sulfur or selenium may be used in combination with metal cocatalyst, which can optionally be supported on inert carriers.

Among the preferred catalysts are those in which the sulfur or selenium or their compounds are incorporated into palladium or platinum catalysts. Other metal catalysts containing cobalt, iron, nickel and ruthenium and metals in groups IV-B to VII-B such as rhenium may also be used. The sulfur or selenium impregnated metal catalyst, may, if desired, be supported on an inert carrier. Among the preferred inert carrier materials are barium sulfate, clay, diatomaceous earth, calcium sulfate, and charcoal. An especially preferred catalyst is sulfided palladium on charcoal. The advantage obtained by using sulfur impregnated metal catalysts is generally faster rates and higher yields of triaryl phosphine than are obtained with sulfur or selenium or metal catalyst alone.

Generally, the reaction is carried out with amounts of from 0.0001 to 0.5 moles of sulfur or selenium or their compounds per mole of the compound of formula I to be reduced, preferably about 0.001 to 0.05 moles of sulfur or selenium or their compounds per mole of the compound of formula I to be reduced. Use of amounts of sulfur or selenium or their compounds greater than 0.5 moles per mole of the compound of formula I to be reduced is generally avoided because most of the sulfur or selenium used will be present as triaryl phosphine sulfide or triaryl phosphine selenide at the end of the reaction. If sulfur or selenium or their compounds are incorporated into a metal catalyst, the molar ratio of sulfur or selenium to the metal can be from 0.01 to 100 or more with the preferred range being from 0.5 to 50. In this case, the total amount of sulfur or selenium or their compounds can be from 0.0001 to 0.5 moles per mole of the compound of formula I to be reduced. The preferred range is from 0.001 to 0.05 moles of sulfur or selenium per mole of the compound of formula I to be reduced.

This reaction can be carried out without the presence of any inert solvent in the reaction medium. However, if desired, an inert organic solvent can be utilized. Any conventional inert organic solvent can be utilized in carrying out this reaction. Among the preferred inert organic solvents are the aromatic hydrocarbon solvents such as toluene, xylene, benzene, chlorinated hydrocarbon solvents, such as chlorobenzene and hydrocarbon solvents such as hexane and cyclohexane.

The auxiliary agents utilized in the reduction with hydrogen are the tetrahalosilanes. Among the preferred auxiliary agents is silicon tetrachloride. The auxiliary agents are utilized in an amount of at least 0.25 moles per mole of the compound of formula I to be reduced with hydrogen. Generally, it is preferred to utilize the auxiliary agent in an amount of from about 1 mole to about 10 moles per mole of the compound of formula I to be reduced. However, if desired, amounts of greater than 10 moles of the auxiliary agent per mole of the compound of formula I to be reduced can be utilized. However, the use of these large amounts provides no additional benefit and results in added costs in carrying out this reaction.

In carrying out this reaction, conventional hydrogenation conditions are utilized. Generally, this reaction can be carried out at a temperature of from 50°C. to 400°C., with temperatures of 100°C. to 300°C. being especially preferred. The reduction with hydrogen is carried out under pressure. In carrying out this reaction, pressures of from 100 p.s.i.g. to 2,000 p.s.i.g. may be used. In accordance with a preferred embodiment of this invention, this pressure is obtained by pumping hydrogen gas into the reaction medium containing the compound of formula I, the auxiliary agent and the catalyst in a closed system such as an autoclave. If desired, an inert organic solvent may also be present.

The reduction with hydrogen is carried out for a period of at least 5 minutes. Generally, it is preferred, for best yields, to carry out this reaction for a period of 10 minutes to 48 hours or longer. While reaction times of greater than 48 hours, i.e., up to 20 days or even longer can be utilized, the use of these long reaction times usually provides no additional benefits and adds to the cost of the reaction. Therefore, these long reaction times are seldom utilized.

The following examples are illustrative but not limitative of the invention. In the examples, all temperatures are in degrees centigrade.

The sulfided palladium on carbon utilized in the examples designates a catalyst containing about 5% by weight of a mixture of palladium and palladium sulfide and about 95% by weight carbon. This mixture of palladium and palladium sulfide contained about 36% by weight palladium sulfide and about 64% by weight palladium.

EXAMPLE 1

To an oven-dried 50-ml autoclave liner were added 16.68 g of triphenylphosphine oxide (.06 mole) and 0.057 g of sulfur (.0018 mole). The solids were treated with 11.12 g of silicon tetrachloride (.066 mole) and the mixture was placed in an autoclave which was then charged to a pressure of 715 p.s.i.g. (48 atm.) with hydrogen. The mixture was heated to 250°C for 15 hours at a maximum pressure of 77 atm. After cooling and venting, the reaction mixture was worked up by first partitioning between warm 30% by weight aqueous sodium hydroxide solution and toluene. The aqueous layer was extracted once with toluene and the combined organic layers were washed with water and with brine and dried over anhydrous sodium sulfate. Filtration and solvent removal gave 13.66 g (86.9%) of crude triphenylphosphine, mp 68°–77° which contained 2% triphenylphosphine oxide and 3% triphenylphosphine sulfide by gas-liquid chromatographic (glc) analysis. Recrystallization from methanol gave 11.25 g (71%) of purified triphenylphosphine, mp 75°–9°, still containing 1-2% triphenylphosphine sulfide by glc analysis.

EXAMPLE 2

To an oven-dried 50-ml autoclave liner were added 2.78 g of triphenylphosphine oxide (.01 mole), 0.102 g of triphenylphosphine selenide ($3 \times 10^{-4}$ mole), and 2.96 g of silicon tetrachloride (.017 mole). The mixture was heated for 10 hours at 150° in an autoclave under an initial pressure of 700 p.s.i.g. of hydrogen. After workup as in Example 1, 2.76 g (98%) of crude product containing, by glc analysis, 15% triphenylphosphine, 80% triphenylphosphine oxide, and 3% triphenylphosphine selenide was obtained.

EXAMPLE 3

To an oven-dried 50-ml autoclave liner were added 16.68 g of triphenylphosphine oxide (0.06 mole), 0.096 g of sulfur (.003 mole), and 11.12 g of silicon tetrachloride (0.066 mole). The mixture was heated for 65 hours at 180°C in an autoclave under an initial pressure of 700 p.s.i.g. of hydrogen and a maximum pressure of 995 p.s.i.g. After workup as in Example 1, 14.66 g (93%) of crude product containing, by glc analysis, 90% triphenylphosphine, 5% triphenylphosphine oxide and 5% triphenylphosphine sulfide was obtained.

EXAMPLE 4

To an oven-dried 50-ml autoclave liner were added 5.56 g of triphenylphosphine oxide (0.02 mole), 0.294 g of triphenylphosphine sulfide (0.001 mole), and 3.71 g of silicon tetrachloride (0.022 mole). The mixture was heated for 15 hours at 200°C in an autoclave under an initial pressure of 700 p.s.i.g. of hydrogen. After workup as in Example 1, 5.59 g (100%) of crude product containing, by glc analysis, 70% triphenylphosphine, 25% triphenylphosphine oxide, and 5% triphenylphosphine sulfide was obtained.

EXAMPLE 5

To an oven-dried 50-ml autoclave liner were added 16.68 g of triphenylphosphine oxide (.06 mole), 0.018 g of sulfur (.00057 mole), 0.129 of 5% palladium-on-carbon (6 × $10^{-5}$ g-atom of palladium), and 11.12 g of silicon tetrachloride (.066 mole). The mixture was heated for 10 hours at 150°C in an autoclave under an initial pressure of 700 p.s.i.g. of hydrogen. The reaction mixture was worked up by first cooling and venting the reaction mixture, which was then partitioned between warm 30% by weight aqueous sodium hydroxide solution and toluene. The catalyst was recovered by filtration and the aqueous layer of the filtrate was extracted once with toluene. The combined toluene layers were washed with water and with brine and dried over anhydrous sodium sulfate. Solvent removal gave 15.20 g (96.6%) of pale yellow crystals, mp 77°–80°. Analysis by glc indicated the presence of triphenylphosphine, triphenylphosphine oxide, and triphenylphosphine sulfide in a 98:1:1 ratio.

EXAMPLE 6

To an oven-dried 50-ml autoclave liner were added 5.56 g of crude, water-wet triphenyl-phosphine oxide (0.02 mole), 1.1 g of 5% by weight sulfided palladium-on carbon, and 20 ml of toluene. The mixture was heated to boiling and 10 ml of distillate containing the toluene-water azeotrope was collected. The residual solution was treated with 3.4 g of silicon tetrachloride (.02 mole). The mixture was heated for 18 hours at 110°C in an autoclave under an initial pressure of 200 p.s.i.g. (14 atm.). Workup as in Example 5 provided a crude product which by glc analysis contained 72% triphenylphosphine, 27% triphenylphosphine oxide, and 1% triphenylphosphine sulfide.

A 61 g sample of material prepared similarly (glc assay 91% triphenylphosphine) was allowed to react with 48.2 g of 91.6% pure vinyl-β-ionol in methanol-pyridine containing concentrated hydrochloric acid. After crystallization from ethyl acetate, there were obtained 92.6 g (92.6% yield) of C-15 Wittig salt, useful in the preparation of Vitamin A.

EXAMPLE 7

To an oven-dried 50-ml autoclave liner were added 3.60 g of triphenylphosphine oxide (.013 mole), 0.132 g of triphenylphosphine selenide (3.9 × $10^{-4}$ mole), 0.030 g of 5% palladium-on-carbon, and 2.37 g of silicon tetrachloride (0.0139 mole). The mixture was heated for 10 hours at 150° in an autoclave under an initial pressure of 700 p.s.i.g. of hydrogen. Workup as in Example 5 provided 3.48 g of crude product which contained, by glc analysis, 55% triphenylphosphine, 42% triphenylphosphine oxide, and 3% triphenylphosphine selenide.

EXAMPLE 8

To an oven-dried 50 ml. autoclave liner were added 5.56 g. of triphenylphosphine oxide (20 mmols) and 1.35 g. of 5% by weight platinum sulfide on 95% by weight of carbon (ca. 1.5 mol % Pt.). To these solids were added 20 ml. of toluene and 6.8 g. (4.6 ml.) of silicon tetrachloride (40 mmols). The mixture was placed in an autoclave and charged to a pressure of 500 p.s.i.g. (34 atm.) with hydrogen. The mixture was heated at 140°–150°C. for 18 hours at a maximum pressure of 49 atm. After cooling and venting, the reaction mixture was partitioned between 100 ml. of 1N aqueous sodium hydroxide and 200 ml. of diethyl ether. Filtration and rinsing with an additional 200 ml. of diethyl ether provided, after drying, 1.30 g. of catalyst suitable for reuse. The organic layer of the two-phase filtrate was separated and washed with 2 × 100 ml. of water and 1 × 100 ml. of brine, followed by drying over 10 g. of sodium sulfate. Solvent removal on the rotary evaporator left 5.10 g. (97%) of pale yellow crystals. Analysis by glc revealed the presence of triphenylphosphine (95%) triphenylphosphine oxide (4%), and triphenylphosphine sulfide (1%).

We claim:

1. A process for producing a tertiary aryl phosphine from the corresponding tertiary aryl phosphine oxide comprising reacting said phosphine oxide with hydrogen in the presence of sulfur or selenium catalyst, said reaction being carried out in the presence of silicon tetrahalide as an auxiliary agent, said reaction taking place at a temperature of from 50°C. to 400°C. and pressures of from 100 p.s.i.g. to 2000 p.s.i.g.

2. The process of claim 1 wherein said auxiliary agent is present in an amount of at least 0.25 moles per mole of said phosphine.

3. The process of claim 2 wherein said auxiliary agent is silicon tetrachloride.

4. The process of claim 1 wherein the catalyst is sulfur or selenium incorporated into a metal catalyst.

5. The process of claim 4 wherein the metal catalyst is palladium on a carbon support.

6. The process of claim 5 wherein said auxiliary agent is present in an amount of at least 0.5 moles per mole of said phosphine.

7. The process of claim 6 wherein said auxiliary agent is silicon tetrachloride.

8. The process of claim 1 wherein said catalyst is a compound capable of acting as a sulfur or selenium atom donor which is incorporated in a palladium catalyst.

9. The process of claim 8 wherein said compound is triphenyl phosphine sulfide.

10. The process of claim 1 wherein said catalyst is elemental sulfur.

11. The process of claim 1 wherein said catalyst is elemental selenium.

12. The process of claim 1 wherein said catalyst is present as a compound capable of acting as a sulfur or selenium atom donor.

13. The process of claim 12 wherein said catalyst is triphenyl phosphine sulfide.

14. The process of claim 12 wherein said catalyst is triphenyl phosphine selenide.

* * * * *